United States Patent
Kurose

(10) Patent No.: US 10,130,777 B2
(45) Date of Patent: Nov. 20, 2018

(54) INJECTION NEEDLE

(71) Applicant: TERUMO KABUSHIKI KAISHA, Tokyo (JP)

(72) Inventor: Katsutoshi Kurose, Tokyo (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 29 days.

(21) Appl. No.: 15/081,479

(22) Filed: Mar. 25, 2016

(65) Prior Publication Data

US 2016/0206832 A1 Jul. 21, 2016

Related U.S. Application Data

(63) Continuation of application No. PCT/JP2015/065023, filed on May 26, 2015.

(30) Foreign Application Priority Data

Jul. 8, 2014 (JP) .................. 2014-140774

(51) Int. Cl.
*A61M 5/32* (2006.01)
*A61F 9/007* (2006.01)

(52) U.S. Cl.
CPC .......... *A61M 5/3286* (2013.01); *A61F 9/007* (2013.01); *A61F 9/00736* (2013.01)

(58) Field of Classification Search
CPC .. A61M 5/3286; A61M 5/158; A61F 9/00736
See application file for complete search history.

(56) References Cited

U.S. PATENT DOCUMENTS

| | | | |
|---|---|---|---|
| 5,752,942 A * | 5/1998 | Doyle ................. | A61M 5/3286 604/274 |
| 2005/0107751 A1 | 5/2005 | Yatabe et al. | |
| 2014/0296797 A1* | 10/2014 | Iwase ................. | A61M 5/3286 604/272 |
| 2016/0317757 A1* | 11/2016 | Ooyauchi ............. | A61M 5/158 |

FOREIGN PATENT DOCUMENTS

| | | |
|---|---|---|
| JP | 2003-511204 A | 3/2003 |
| JP | 2003-290354 A | 10/2003 |
| JP | 2009-508593 A | 3/2009 |
| WO | WO-01/028473 A1 | 4/2001 |
| WO | WO-2007/035621 A1 | 3/2007 |

OTHER PUBLICATIONS

International Search Report for PCT/JP2015/065023 dated Jul. 7, 2015.

\* cited by examiner

*Primary Examiner* — Rebecca E Eisenberg
(74) *Attorney, Agent, or Firm* — Foley & Lardner LLP

(57) ABSTRACT

An injection needle includes a needle tube having a proximal end and a distal end, and an edge surface provided at the distal end of the needle tube. The edge surface includes a first ground facet, a second ground facet, and a third ground facet. The first ground facet is located at a position proximal to the second ground facet and the third ground facet. The second ground facet and the third ground facet converge to form a needle point that is offset from a central plane that perpendicularly crosses the first ground facet and includes a central axis of the needle tube. A length of the edge surface is 0.6 to 2.2 mm. An outside diameter of the needle tube is 0.18 to 0.6 mm. A ratio of the outside diameter of the needle tube to the length of the edge surface is 0.265 to 0.325.

6 Claims, 2 Drawing Sheets

INJECTION NEEDLE

CROSS-REFERENCE TO RELATED APPLICATIONS

This application is a continuation application filed under 35 U.S.C. 111(a) claiming the benefit under 35 U.S.C. §§ 120 and 365(c) of PCT International Application No. PCT/JP2015/065023, filed on May 26, 2015, which claims priority to Japanese Patent Application No. 2014-140774, filed on Jul. 8, 2014. The contents of these applications are hereby incorporated by reference in their entireties.

BACKGROUND

The present disclosure relates to an injection needle that reduces the risk of tissue damage during injection, and more particularly, to an injection needle that can be used in cosmetic surgery and ophthalmic surgery.

Various medical injection needles are currently proposed. In ophthalmic surgery, a procedure of injecting gas or liquid into the anterior chamber of the eyeball, the vitreous chamber, or the fundus of the eye is performed during or after the surgery. For example, in treatment for age-related macular degeneration, anti-VEGF antibody administration is performed by intravitreal injection. JP 2009-508593 W proposes an apparatus for intravitreal injection.

The apparatus for intravitreal injection of JP 2009-508593 W includes: a syringe including a barrel having a proximal end and a distal end, and a volume of 1 mL or less, the barrel being adapted to contain an injection solution, the solution containing a sub-visible particulate count of less than 50 particles per mL when contained in the barrel; a Luer lock tip attached to the distal end of the barrel; a needle having a gauge of 27 or narrower, the needle including a cannula attached to a Luer lock hub for attachment to the Luer lock tip, the needle requiring a penetration force of less than 100 g to penetrate scleral tissue; a syringe tip cap attached to the Luer lock tip for sealing a solution contained in the barrel; and a needle tip shield adapted to attach to the Luer lock hub and enclose the needle.

SUMMARY

The above administration by injection in ophthalmic surgery brings a feeling of fear to a patient. Further, for example, when intravitreal injection is performed, there is the risk of serious visual impairment caused by bacterial endophthalmitis when bacteria enter a wound generated by the injection.

In the apparatus for intravitreal injection of JP 2009-508593 W, the cannula of 30 gauge is used, and the cannula is coated with silicone. However, this structure is not enough to eliminate the above risk in intravitreal injection. Further, the field of cosmetic surgery also faces the problem of tissue damage caused by a syringe.

It is an object of certain embodiments of the present invention to provide an injection needle that can solve the above problems associated with the conventional techniques and reduce the risk of tissue damage during injection.

In order to solve the above issue, certain embodiments of the present invention provide an injection needle including: a needle tube; a first ground facet formed on a distal end of the needle tube; and at least two ground facets subsequently formed on the needle tube to form a needle point, wherein the needle point is not present on (i.e., is offset from) a central plane that perpendicularly crosses the first ground facet and includes a central axis of the needle tube. A length (A) in a central axis direction of an edge surface including the first ground facet and the at least two ground facets is in the range of 0.6 to 2.2 mm. An outside diameter (L) of the needle tube is in the range of 0.18 to 0.6 mm. A ratio of the outside diameter (L) of the needle tube to the length (A) is in the range of 0.265 to 0.325.

Certain embodiments of the present invention provide an injection needle including: a needle tube; and an edge surface including three ground facets formed on a distal end of the needle tube to provide a needle point, wherein when one of the ground facets that is remotest from the needle point is defined as a first ground facet, and the other ground facets are defined as a second ground facet and a third ground facet. An angle $\alpha$ is formed between the first ground facet and a central axis of the needle tube. An angle is formed between the second ground facet and the central axis of the needle tube. An angle $\theta$ is formed between the third ground facet and the central axis of the needle tube. The angles have the relationships: $\alpha<\phi$, $\alpha<\theta$, and $\phi \neq \theta$. L represents an outside diameter of the needle tube, A represents a length in a central axis direction of the first ground facet, $C_1$ represents a length of the second ground facet, and $C_2$ represents a length of the third ground facet. The outside diameter (L) of the needle tube is in the range of 0.18 to 0.6 mm. A ratio of the outside diameter (L) of the needle tube to the length (A) is in the range of 0.265 to 0.325. A ratio of the outside diameter (L) of the needle tube to the length ($C_1$) is in the range of 0.45 to 0.52. A ratio of the outside diameter (L) of the needle tube to the length ($C_2$) is in the range of 0.83 to 1.2.

The injection needle according to certain embodiments of the present invention may be used in at least either retrobulbar administration or Tenon's capsule administration.

The injection needle according to certain embodiments of the present invention can reduce the risk of tissue damage during injection and can be suitably used in cosmetic surgery and ophthalmic surgery.

DETAILED DESCRIPTION

An injection needle according to the present invention will be described in detail on the basis of a preferred embodiment illustrated in the accompanying drawings.

Figure 1B:
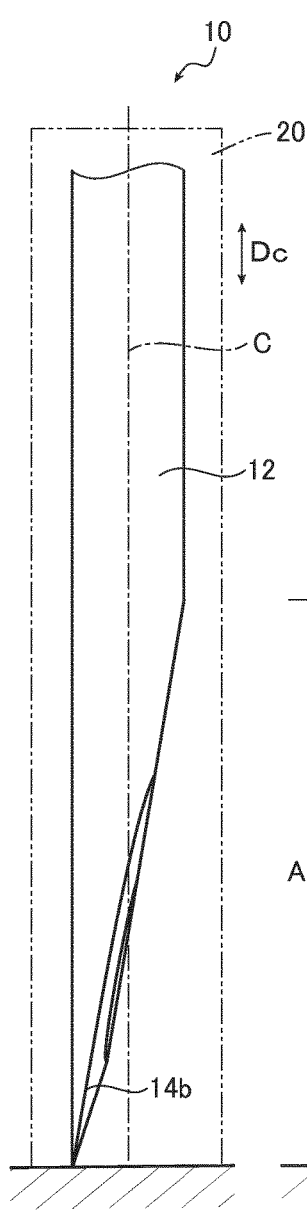
FIG. 1B is a left side view of the injection needle according to the embodiment of FIG. 1A.
Figure 1A:
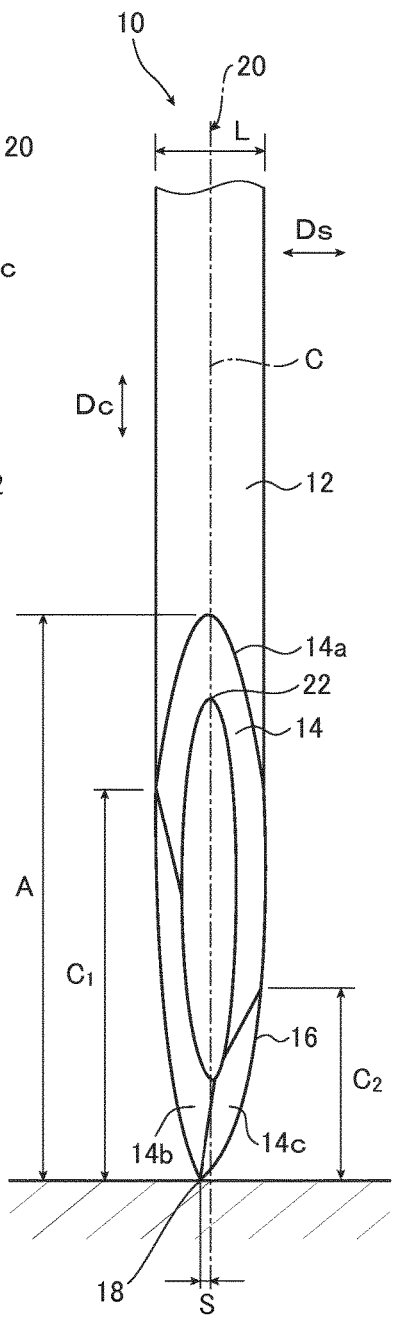
FIG. 1A is a plan view of an injection needle according to an embodiment of the present invention.
Figure 1C:
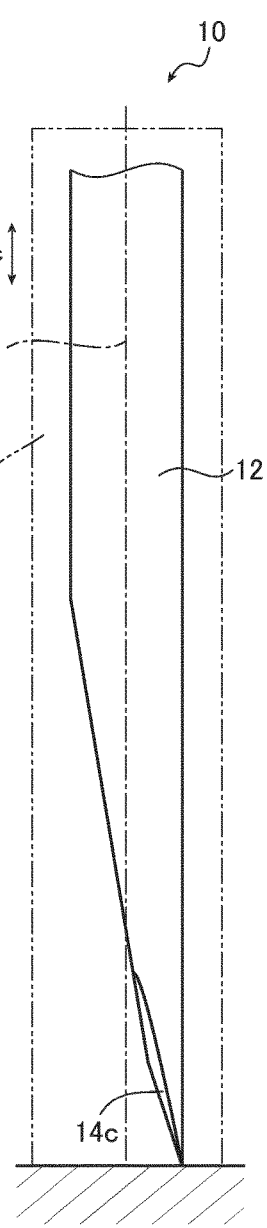
FIG. 1C is a right side view of the injection needle according to the embodiment of FIG. 1A.

As illustrated in FIG. 1A, an injection needle 10 has a needle tube 12 including an edge surface 14 formed on the distal end. The edge surface 14 includes a first ground facet 14a which is positioned furthest from a needle point 18, a second ground facet 14b, and a third ground facet 14c. The injection needle 10 is formed in such a manner that, in the edge surface 14, the needle point 18 is not present on a central plane 20 (see FIGS. 1B and 1C), which perpendicularly crosses the first ground facet 14a and includes a central axis C of the needle tube 12.

A length A in a central axis direction Dc of the edge surface 14 is in the range of 0.6 to 2.2 mm. When the length A in the central axis direction Dc of the edge surface 14 is in the range of 0.6 to 2.2 mm, the angle of the edge surface 14 can be increased. Accordingly, when a drug is delivered by injection, the insertion depth into a target tissue can be reduced, which enables the risk of damaging the target tissue by the injection to be reduced. The length A in the central axis direction Dc of the edge surface 14 is preferably in the range of 0.62 to 0.90 mm.

As used herein, the term "target tissue" indicates a region in a living body to be injected, and is not particularly limited to any region. Examples of the target tissue include the skin, the vitreous body, the anterior chamber of the eyeball, the vitreous chamber, the fundus of the eye, and the Tenon's capsule.

The needle tube 12 is a 23 gauge to 34 gauge needle tube. In this case, an outside diameter (L) of the needle tube 12 is in the range of 0.18 mm to 0.6 mm. When the outside diameter (L) of the needle tube 12 falls out of the range of 0.18 mm to 0.6 mm, defective conditions occur. In particular, when the outside diameter (L) is larger than the range of 0.18 mm to 0.6 mm, a possibility of damaging the target tissue is expanded. On the other hand, when the outside diameter (L) is smaller than the range of 0.18 mm to 0.6 mm, it is difficult to process the tip. The needle tube 12 is preferably in the range of 32 gauge to 33 gauge, in which case, the outside diameter (L) of the needle tube 12 is in the range from 0.20 mm to 0.23 mm. More preferably, the needle tube 12 is 32.5 gauge.

A value of dividing the outside diameter (L) of the needle tube 12 by the length (A) in the central axis direction Dc of the edge surface 14 (L/A) is set in the range of 0.265 to 0.325. When L/A is larger than the range of 0.265 to 0.325, it is difficult to puncture a target. On the other hand, when L/A is smaller than the range of 0.265 to 0.325, the edge surface becomes too long, which increases the risk of damaging a target. More preferably, L/A is set in a range of 0.28 to 0.30.

The needle tube 12 may be made of, for example, an iron material including stainless steel; a non-ferrous metal material such as aluminum, copper, or titanium; a heat-resistant material such as nickel, cobalt, or molybdenum; a metal having a low melting point such as lead or tin; a precious metal material such as gold, silver, or platinum; or an alloy thereof.

The needle tube 12 may be shaped not only as a straight tube, but also as a tapered tube whose outside diameter decreases toward the distal end or the proximal end. The needle tube 12 may have a tapered shape in part of the edge surface 14. The edge surface 14 of the needle tube 12 may be coated with silicone to reduce the resistance during injection.

In the injection needle 10, forming the edge surface 14 in the shape described above results in a projecting shape of an edge 16 formed by the third ground facet 14c. Accordingly, when the injection needle 10 is brought into contact with a target tissue such as the skin or vitreous body via the needle point 18, a portion making contact with the target tissue is not a point, but more like a line. Thus, forces that are applied to the target tissue can be sufficiently distributed. As a result, it is possible to smoothly puncture the target tissue, and thereby reduce pain. The projecting direction of the edge 16 is not particularly limited to any direction, and may be, for example, the direction of the second ground facet 14b. That is, the needle point 18 may be positioned on either side of the central plane 20.

A minimum distance S between the needle point 18 and the central plane 20 is preferably in the range of 3 to 20% of the maximum outside diameter of the edge surface 14 in a minor axis direction Ds (see FIG. 1A), and more preferably in the range of 5 to 15% of the maximum outside diameter of the edge surface 14 in the minor axis direction Ds. The minimum distance S between the needle point 18 and the central plane 20 is preferably in the range of 8 to 100 μm, and more preferably in the range of 8 to 35 μm.

When the minimum distance S between the needle point 18 and the central plane 20 is smaller than the range of 8 to 100 μm, a portion of the edge 16 that makes initial contact with the target tissue is closer to being a point than a line. Thus, forces that are applied to the target tissue cannot be sufficiently distributed. Accordingly, the target tissue cannot be smoothly punctured, and a patient feels pain. On the other hand, when the minimum distance S between the needle point 18 and the central plane 20 is larger than the range of 8 to 100 μm, a portion of the edge 16 that contacts the target tissue becomes larger, which makes it difficult for the needle point 18 to penetrate the target tissue. Thus, the target tissue cannot be smoothly punctured, and a patient may feel even more pain.

Figure 2A:
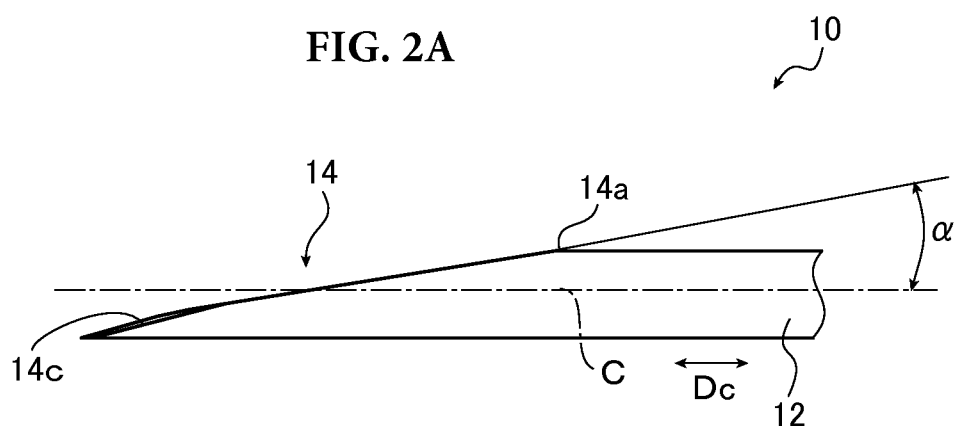
FIGS. 2A to 2C are rotated side views of the injection needle according to the embodiment of FIG. 1A, FIG. 2A being a side view of the injection needle with a first ground facet being viewed flush with line of sight, FIG. 2B being a side view of the injection needle with a second ground facet being viewed flush with line of sight, and FIG. 2C being a side view of the injection needle with a third ground facet being viewed flush with line of sight.
Figure 2B:
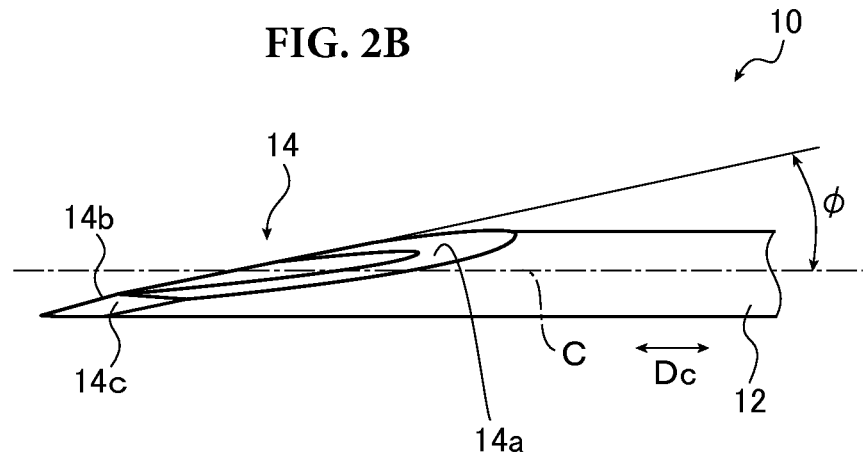
Figure 2C:
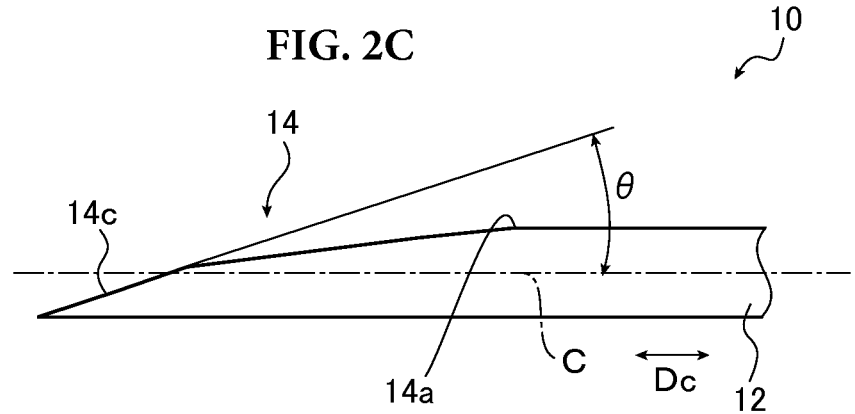

The injection needle 10 according to the embodiment of the present invention will further be described in detail with reference to FIGS. 2A to 2C. FIGS. 2A to 2C are side views of the injection needle according to the embodiment of FIG. 1A. FIG. 2A is a side view of the injection needle with the first ground facet 14a being viewed flush with line of sight. FIG. 2B is a side view of the injection needle with the second ground facet 14b being viewed flush with line of sight. FIG. 2C is a side view of the injection needle with the third ground facet 14c being viewed flush with line of sight.

As illustrated in FIG. 2A, in the edge surface 14, the first ground facet 14a forms an angle α with respect to the central axis C of the needle tube 12. As illustrated in FIG. 2B, the second ground facet 14b forms an angle φ with respect to the central axis C of the needle tube 12. As illustrated in FIG. 2C, the third ground facet 14c forms an angle θ with respect to the central axis C of the needle tube 12. The angle φ and the angle θ are larger than the angle α. The angle θ and the angle φ are different from each other. That is, these angles satisfy the following relationships: $\alpha<\phi$, $\alpha<\theta$, and $\phi\neq\theta$.

The angles α, φ and θ are preferably set so that the needle point 18 perpendicularly crosses the first ground facet 14a, and the minimum distance S between the needle point 18 and the central plane 20 including the central axis C of the needle tube 12 is in the range of 3 to 20% of the maximum outside diameter in the minor axis direction Ds (see FIG. 1A) of the edge surface 14, and more preferably, in the range of 5 to 15% of the maximum outside diameter. The minimum distance S (see FIG. 1A) between the needle point 18 and the central plane 20 is preferably set in the range of 8 to 100 μm, and more preferably set in the range of 8 to 35 μm.

When the minimum distance S is smaller than the range of 8 to 100 μm, a portion of the edge 16 that makes initial contact with the target tissue is closer to being a point than a line. Thus, forces that are applied to the target tissue cannot be sufficiently distributed. Accordingly, the target tissue cannot be smoothly punctured, and a patient feels pain. On the other hand, when the minimum distance S is larger than the range of 8 to 100 μm, a portion of the edge 16 that contacts the target tissue becomes larger, which makes it difficult for the needle point 18 to penetrate the target tissue (e.g., the skin). Thus, the target tissue cannot be smoothly punctured, and a patient may feel even more pain.

A length $C_1$ in the central axis direction Dc of the second ground facet 14b and a length $C_2$ in the central axis direction Dc of the third ground facet 14c are preferably set to 20% or more and 80% or less of the length A in the central axis direction Dc of the edge surface 14. When the length $C_1$ in the central axis direction Dc of the second ground facet 14b and the length $C_2$ in the central axis direction Dc of the third ground facet 14c is less than 20% of the length A in the central axis direction Dc of the edge surface 14, an area of the injection needle that is capable of puncturing the target tissue is reduced. Thus, it is difficult to insert the injection needle 10. On the other hand, when the length $C_1$ in the central axis direction Dc of the second ground facet 14b and the length $C_2$ in the central axis direction Dc of the third ground facet 14c is larger than 80% of the length A in the central axis direction Dc of the edge surface 14, a sharp projection is formed inside a jaw 22, and a patient feels more pain. Thus, lengths outside of the range discussed above are unsuitable.

In the injection needle 10 illustrated in FIG. 1A, the length $C_1$ in the central axis direction Dc of the second ground facet 14b is longer than the length $C_2$ in the central axis direction Dc of the third ground facet 14c. However, the present embodiment is not limited thereto. The length $C_2$ in the central axis direction Dc of the third ground facet 14c may be longer than the length $C_1$ in the central axis direction Dc of the second ground facet 14b. Also in this case, an effect similar to the effect of the injection needle 10 illustrated in FIG. 1A can be obtained.

As described above, in the injection needle 10 according to the present embodiment, since a 23 gauge to 34 gauge is used as the needle tube 12, and the needle point 18 is not present on the central plane 20 which includes the central axis C of the needle tube 12, the target tissue can be smoothly punctured. Further, since the length A in the central axis direction Dc of the edge surface 14 is set in the range of 0.6 to 2.2 mm, and a value of dividing the outside diameter (L) of the needle tube 12 by the length (A) in the central axis direction Dc of the edge surface 14 (L/A) is set in the range of 0.265 to 0.325, the target tissue can be smoothly punctured, and the insertion depth can be reduced. Accordingly, it is possible to reduce the generation of pain during injection, reduce the risk of tissue damage, and reduce the risk of bleeding. Thus, the injection needle 10 can be suitably used in, for example, ophthalmic surgery. For example, the injection needle 10 can reduce the risk of bacterial infection which may occur in intravitreal injection and reduce the generation of pain which may occur in subconjunctival administration. Further, the injection needle 10 can also reduce the risk of bleeding which may occur in retrobulbar administration and Tenon's capsule administration. Thus, the injection needle 10 can be suitably used in retrobulbar administration and Tenon's capsule administration Further, the outside diameter (L) of the needle tube 12 preferably has the following relationships with the length A in the central axis direction Dc of the first ground facet 14a, the length $C_1$ in the central axis direction Dc of the second ground facet 14b, and the length $C_2$ in the central axis direction Dc of the third ground facet 14c: 1) a value of the outside diameter (L) of the needle tube 12/the length (A) is in the range of 0.265 to 0.325, 2) a value of the outside diameter (L) of the needle tube 12/the length ($C_1$) is in the range of 0.45 to 0.52, and 3) a value of the outside diameter (L) of the needle tube 12/the length ($C_2$) is in the range of 0.83 to 1.2. These length relationships enable the puncture into a target tissue to be smoothly performed and the insertion depth to be reduced. More preferably, a value of A is in the range of 0.62 to 0.9 mm, a value of L/A is in the range of 0.28 to 0.30, a value of L/$C_1$ is in the range of 0.5 to 0.52, and a value of L/$C_2$ is in the range of 0.9 to 1.1.

Examples of the injection needle of according to the embodiments of the present invention are described in the following TABLE 1. The values in TABLE 1 indicate the relationships between the gauge of the needle tube 12, the outside diameter L of the needle tube 12, the length A in the central axis direction Dc of the edge surface 14, the length $C_1$ in the central axis direction Dc of the second ground facet 14b, and the length $C_2$ in the central axis direction Dc of the third ground facet 14c. The configuration shown in the following TABLE 1 enables manufacture of the injection needle according to an embodiment of the present invention.

TABLE 1

| GAUGE | NEEDLE TUBE OUTSIDE DIAMETER L (mm) | FIRST GROUND FACET LENGTH A (mm) | SECOND GROUND FACET LENGTH $C_1$ (mm) | THIRD GROUND FACET LENGTH $C_2$ (mm) | L/A | L/$C_1$ | L/$C_2$ |
|---|---|---|---|---|---|---|---|
| 23 | 0.6 | 2.2 | 1.3 | 0.6 | 0.27 | 0.46 | 1.0 |
| 24 | 0.55 | 1.9 | 1.1 | 0.6 | 0.29 | 0.5 | 0.92 |
| 25 | 0.5 | 1.7 | 1.0 | 0.5 | 0.29 | 0.5 | 1.0 |
| 26 | 0.45 | 1.5 | 0.9 | 0.4 | 0.3 | 0.5 | 1.1 |
| 27 | 0.4 | 1.4 | 0.8 | 0.4 | 0.29 | 0.5 | 1.0 |
| 28 | 0.36 | 1.2 | 0.7 | 0.3 | 0.3 | 0.51 | 1.2 |
| 29 | 0.33 | 1.1 | 0.7 | 0.3 | 0.3 | 0.47 | 1.1 |
| 30 | 0.3 | 1.0 | 0.6 | 0.3 | 0.3 | 0.5 | 1.0 |
| 31 | 0.25 | 0.9 | 0.5 | 0.3 | 0.28 | 0.5 | 0.83 |
| 32 | 0.23 | 0.8 | 0.5 | 0.2 | 0.29 | 0.46 | 1.15 |
| 33 | 0.2 | 0.7 | 0.4 | 0.2 | 0.29 | 0.5 | 1.0 |
| 34 | 0.18 | 0.6 | 0.4 | 0.2 | 0.3 | 0.45 | 0.9 |

The injection needle according to certain embodiments of the present invention has been described in detail above. However, the embodiments described above are illustrative only, and not limiting. Those skilled in the art who review this disclosure will readily appreciate that various improvements and modifications may be made without departing from the scope of the invention.

REFERENCE SIGNS LIST 10 injection needle
12 needle tube 14 edge surface
14a first ground facet
14b second ground facet
14c third ground facet
16 edge
18 needle point
20 central plane
22 jaw
A length in a central axis direction of the edge surface
$C_1$ length of the second ground facet
$C_2$ length of the third ground facet
C central axis
L outside diameter
S minimum distance

What is claimed is:

1. An injection needle comprising:
a needle tube having a proximal end and a distal end; and
an edge surface provided at the distal end of the needle tube, the edge surface comprising a first ground facet, a second ground facet, and a third ground facet,
wherein the first ground facet is located at a position proximal to the second ground facet and the third ground facet,
wherein the second ground facet and the third ground facet converge to form a needle point,
wherein the needle point is offset from a central plane that perpendicularly crosses the first ground facet and includes a central axis of the needle tube,
wherein an outside diameter of the needle tube is in a range of 0.18 to 0.6 mm,
wherein a length of the edge surface measured in a central axis direction is in a range of 0.62 to 0.90 mm,
wherein a ratio of the outside diameter of the needle tube to the length of the edge surface measured in the central axis direction is in a range of 0.28 to 0.30,
wherein a ratio of the outside diameter of the needle tube to a length of the second ground facet measured in the central axis direction is in a range of 0.5 to 0.52, and
wherein a ratio of the outside diameter of the needle tube to a length of the third ground facet measured in the central axis direction is in a range of 0.9 to 1.1.

2. The injection needle of claim 1, wherein
an angle $\alpha$ is formed between the first ground facet and the central axis of the needle tube, an angle $\phi$ is formed between the second ground facet and the central axis of the needle tube, and an angle $\theta$ is formed between the third ground facet and the central axis of the needle tube, and
the angles $\alpha$, $\phi$, and $\theta$ satisfy the following relationships:

$\alpha < \phi$, $\alpha < \theta$, and $\phi \neq \theta$.

3. The injection needle according to claim 1, wherein the injection needle is configured to be used in retrobulbar administration.

4. The injection needle according to claim 1, wherein the injection needle is configured to be used in Tenon's capsule administration.

5. A method of performing ophthalmic surgery comprising:
providing an injection needle comprising:
a needle tube having a proximal end, a distal end, and an outside diameter that is in a range of 0.18 to 0.6 mm, and
an edge surface provided at the distal end of the needle tube, the edge surface comprising a first ground facet, a second ground facet, and a third ground facet,
wherein the first ground facet is disposed proximal of the second ground facet and the third ground facet,
wherein the second ground facet and the third ground facet converge to form a needle point,
wherein the needle point is offset from a central plane that perpendicularly crosses the first ground facet and includes a central axis of the needle tube,
wherein a length of the edge surface measured in a central axis direction is in a range of 0.62 to 0.90 mm,
wherein an outside diameter of the needle tube is in a range of 0.18 to 0.6 mm, wherein a ratio of the outside diameter of the needle tube to the length of the edge surface measured in the central axis direction is in a range of 0.28 to 0.30,
wherein a ratio of the outside diameter of the needle tube to a length of the second ground facet measured in the central axis direction is in a range of 0.5 to 0.52, and
wherein a ratio of the outside diameter of the needle tube to a length of the third ground facet measured in the central axis direction is in a range of 0.9 to 1.1;
inserting the needle into a target tissue; and
injecting a drug to the target tissue through the injection needle.

6. The method according to claim 5, wherein the ophthalmic surgery is one of intravitreal injection, subconjunctival administration, retrobulbar administration, and Tenon's capsule administration.

* * * * *